(12) United States Patent
Dubois et al.

(10) Patent No.: US 10,039,464 B2
(45) Date of Patent: Aug. 7, 2018

(54) PHASE VALUES AND WAVE FRONT DETECTION FOR ELECTROPHYSIOLOGICAL CARDIAC SIGNALS

(71) Applicant: CARDIOINSIGHT TECHNOLOGIES, INC., Cleveland, OH (US)

(72) Inventors: Remi Dubois, Paris (FR); Qingguo Zeng, Solon, OH (US); Ping Jia, Solon, OH (US); Venkatesh Vasudevan, Beachwood, OH (US); Charulatha Ramanathan, Solon, OH (US)

(73) Assignee: CARDIOINSIGHT TECHNOLOGIES, INC., Cleveland, OH (US)

( * ) Notice: Subject to any disclaimer, the term of this patent is extended or adjusted under 35 U.S.C. 154(b) by 580 days.

(21) Appl. No.: 14/157,991

(22) Filed: Jan. 17, 2014

(65) Prior Publication Data

US 2014/0200822 A1    Jul. 17, 2014

Related U.S. Application Data

(60) Provisional application No. 61/753,792, filed on Jan. 17, 2013.

(51) Int. Cl.
*A61B 5/044* (2006.01)
*A61B 5/04* (2006.01)
(Continued)

(52) U.S. Cl.
CPC ...... *A61B 5/04012* (2013.01); *A61B 5/04011* (2013.01); *A61B 5/0422* (2013.01); *A61B 5/0452* (2013.01); *A61B 5/04085* (2013.01); *G06F 17/5018* (2013.01); *A61B 5/044* (2013.01); *A61B 5/7285* (2013.01); *A61B 5/743* (2013.01); *G06F 2217/16* (2013.01)

(58) Field of Classification Search
None
See application file for complete search history.

(56) References Cited

U.S. PATENT DOCUMENTS

2004/0243018 A1  12/2004  Organ et al.
2010/0069776 A1   3/2010  Greger et al.
(Continued)

FOREIGN PATENT DOCUMENTS

WO    2012092016    7/2012

OTHER PUBLICATIONS

Rogers J M., et al., "Quantitative Techniques for Analyzing High-Resolution Cardiac-Mapping Data", IEEE Engineering in Medicine and Biology Magazine, IEEE Service Center, vol. 17, No. 1, Jan. 1, 1998, p. 62-72.

(Continued)

*Primary Examiner* — G. Steven Vanni
(74) *Attorney, Agent, or Firm* — Tarolli, Sundheim, Covell & Tummino LLP

(57) ABSTRACT

A method to calculate and visualize dynamic wave front propagation of electrical signals on a geometric surface is described. Wave front locations are identified on the geometric surface between each identified pair of adjacent nodes on the geometric surface. A graphical map can be generated to represent the identified wave front locations on at least a portion of the geometric surface.

23 Claims, 5 Drawing Sheets

(51) Int. Cl.
    *G06F 17/50*    (2006.01)
    *A61B 5/0408*    (2006.01)
    *A61B 5/042*    (2006.01)
    *A61B 5/0452*    (2006.01)
    *A61B 5/00*    (2006.01)

(56) References Cited

U.S. PATENT DOCUMENTS

| | | |
|---|---|---|
| 2010/0094274 A1 | 4/2010 | Narayan et al. |
| 2011/0251505 A1 | 10/2011 | Narayan et al. |
| 2012/0108957 A1 | 5/2012 | Desai |
| 2012/0283587 A1 | 11/2012 | Gosh et al. |
| 2012/0296569 A1 | 11/2012 | Shahaf et al. |

OTHER PUBLICATIONS

Rogers J. M., "Combined Phase Singularity and Wavefront Analysis for Optical Maps of Ventricular Fibrillation", IEEE Transactions on Biomedical Engineering, IEEE Service Center, vol. 51, No. 1, Jan. 1, 2004, p. 56-65.

K. Umapathy, et al., "Phase Mapping of Cardiac Fibrillation", Circulation. Arrhythmia and Electrophysiology, vol. 3, No. 1, Feb. 1, 2010, pp. 105-114.

Antoine Herline, et al., "reconstruction of Phase Maps from the Configuration of Phase Singularities in Two-Dimensional Manifolds", Physical Review E. (Statistical, Nonlinear, and Soft Matter Physics), vol. 85, No. 5, May 1, 2012, p. 51916.

Supplementary European Search Report, Applicant: Cardiolnsight Technologies, Inc., European Application No. EP14740830, Date of Completion: Jul. 14, 2016, pp. 1-8.

International Application No. PCT/US2014/012051, International Search Report and Written Opinion; Date of Completion: Apr. 22, 2014; dated May 9, 2014; 10PP.

Chinese Patent Application No. 201480010757.7, Filed Jan. 17, 2014; Title: Wave Front Detection for Electrophysiological Signals; Office Action dated Jul. 31, 2017, Applicant: Cardiolnsight Technologies, Inc.; 10 pp.

PHASE VALUES AND WAVE FRONT DETECTION FOR ELECTROPHYSIOLOGICAL CARDIAC SIGNALS

RELATED APPLICATION

This application claims the benefit of U.S. Provisional Patent Application No. 61/753,792, filed Jan. 17, 2013 and entitled WAVE FRONT DETECTION FOR ELECTROPHYSIOLOGICAL SIGNALS, the entire contents of which is incorporated herein by reference.

TECHNICAL FIELD

This disclosure relates to wave front detection for electrophysiological signals.

BACKGROUND

Electrocardiographic mapping (ECM) is a technology that is used to determine and display heart electrical information from sensed electrical signals. ECM can be performed based on invasive or non-invasive measurements of cardiac electrical activity. Electrophysiology data can be used in the diagnosis and treatment of cardiac arrhythmias.

SUMMARY

This disclosure relates to wave front detection for electrophysiological signals.

In one example, a non-transitory computer-readable medium having instructions executable by a processor can perform a method. The method can include computing phase values for a plurality of nodes distributed across a geometric surface based on data representing the electrical activity for the plurality of nodes over time. The computed phase values for each of the nodes can be evaluated at a given time to identify each pair of adjacent nodes having phase values that encompass a phase threshold. At least one location on the geometric surface, corresponding to a wave front at the given time, can be determined based on the evaluation.

Another example can provide a system that includes a memory and one or more processors. The processor(s) can access the memory and execute instructions that include a wave front analyzer. The wave front analyzer can be programmed to evaluate phase values for each of the plurality of nodes at a given time and identify each pair of adjacent nodes having phase values that encompass a predetermined phase value. The wave front analyzer can store wave front data in the memory to identify wave front locations on the geometric surface that reside between each identified pair of adjacent nodes on the geometric surface.

In another example, a method can include storing electrical data in memory to represent electrical activity for a plurality of nodes distributed across a geometric surface over time. Phase values computed for at least a substantial portion of the plurality of nodes can be evaluated at a given time to identify each pair of adjacent nodes having phase values that encompass a wave front phase value. Wave front locations can be identified on the geometric surface between each identified pair of adjacent nodes on the geometric surface. A graphical map can be generated to represent the identified wave front locations on at least a portion of the geometric surface.

DETAILED DESCRIPTION

This disclosure relates to wave front detection for electrophysiological signals. Systems and methods are disclosed to calculate and visualize dynamic wave front propagation of electrical signals on a geometric surface. For example, the electrophysiological signals can represent electrical activity (e.g., potential) for nodes distributed over a geometric surface, such as corresponding to tissue of a patient. The electrical signals can be converted to phase for each of the nodes in the geometric surface. A phase value can be selected to set a boundary condition for the wave front, such as a phase value that indicates a beginning or end of activation or depolarization. The phases for each of the nodes can be evaluated to identify locations along a wave front boundary based on a phase threshold. Any number of pairs of neighboring nodes meeting such criteria can be identified. A point residing along a line extending between the pair of identified neighboring nodes can be determined as being located on a wave front. For example, the points along a plurality of such lines extending between sets of neighboring nodes can be connected on a graphical map to identify visually the wave front on the geometric surface. This can be performed over a plurality of time intervals (e.g., frames) to construct a time series graphical map depicting movement of the wave front across the surface.

While many examples of wave front detection are disclosed with respect to reconstructed electrograms on a cardiac envelope or cardiac surface, the system and method disclosed herein are equally applicable to any electrical signals for a geometric surface, whether measured directly from a surface or derived from measurements. This concept can be applied on ECG and EGM potentials, which can be used to generate phase information. That is, the system and method disclosed herein can be applied on any temporal phase signal that can be acquired from or calculated for a surface. Moreover, while many examples herein are described in the context of wave front detection and mapping of cardiac electrical signals, it is to be understood that the approaches disclosed herein are equally applicable to other electrophysiological signals, such as electroencephalography, electromyography, electrooculography and the like.

Figure 1:
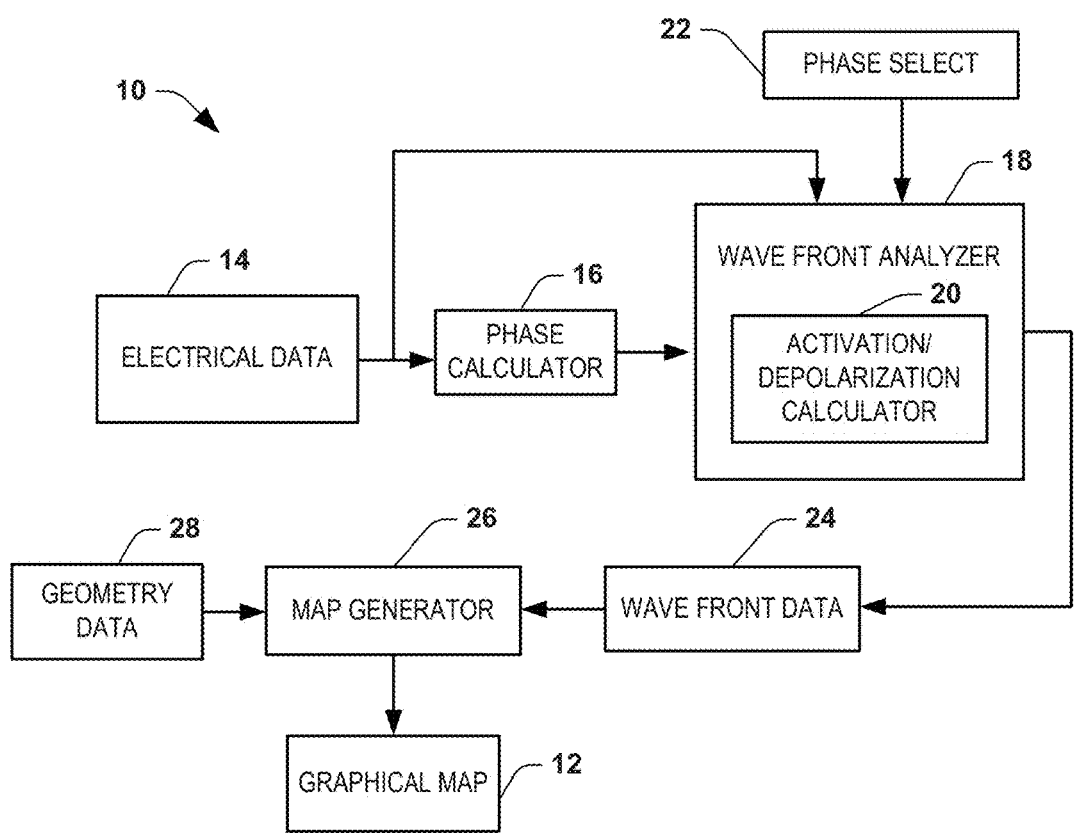
FIG. 1 depicts an example of a system to detect and generate a wave front.

FIG. 1 depicts an example of a system 10 to detect a wave front and to generate a corresponding graphical map 12 (e.g., an electrophysiological map). The system 10 can determine the wave front for a geometric surface based on analysis of electrical data 14. For example, the electrical data 14 can be stored in memory (e.g., one or more non-transitory computer readable media) as electroanatomic data that describes electrical activity at a plurality of anatomical locations over one or more time intervals. For example, the electrical data 14 can be provided as electrograms or other electrical waveforms representing electrical activity for the anatomical locations.

As disclosed herein, the anatomical locations can be represented as nodes distributed over a geometric surface. The geometric surface can be a surface of an anatomical structure, such as tissue of a patient (e.g., human or other animal). In some examples, the patient tissue can be cardiac tissue, such that the geometric surface corresponds to an epicardial surface, an endocardial surface or another cardiac envelope. The geometric surface can be patient specific (e.g., based on imaging data for the patient), it can be a generic model of the surface or it can be a hybrid version of a model that is customized based on patient-specific data (e.g., imaging data, patient measurements, reconstructed data, and/or the like). The electrical data 14 thus can characterize electrical potentials for nodes distributed across any such geometric surface, such as tissue of the patient. As disclosed herein, the geometric surface can be defined by geometry data 28 that is stored in memory.

As a further example, the electrical data 14 can correspond to electrophysiological signals, such as can correspond to physiological signals obtained by one or more electrodes or otherwise derived from such signals. For instance, the electrodes can be applied to measure the electrical activity non-invasively, such as may be positioned over a patient's body surface such as the patient's head (e.g., for electroencephalography), a patient's thorax (e.g., for electrocardiography) or other noninvasive locations. The electrical data thus can correspond to the body surface measured electrical signals or, as disclosed herein, be reconstructed onto another surface based on the body surface measurements. In other examples, the input electrical data 14 can be acquired invasively, such as by one or more electrodes positioned within a patient's body (e.g., on a lead or a basket catheter during an EP study or the like). In yet other examples, the input electrical data 14 can include or be derived from a hybrid approach that includes both non-invasively acquired electrical signals and invasively acquired electrical signals.

The system 10 can include a phase calculator 16 programmed to compute phase of electrical activity for nodes distributed across the geometric surface, corresponding to patient tissue, based on the data representing the electrical activity for the geometric surface over time. In some examples, the geometric surface can be represented as a mesh including a plurality of nodes interconnected by edges to define the mesh. For example the mesh can be implemented as a triangular mesh that interconnects the nodes across the geometric surface of interest. For another example, the mesh can be implemented as rectangular or other polygonal mesh representing geometric surface of interest.

An example of how the computed phase can be determined and phase mapping can be performed is disclosed in PCT Application No. PCT/US13/60851 filed Sep. 20, 2013, and entitled PHYSIOLOGICAL MAPPING FOR ARRHYTHMIA, which is incorporated herein by reference. Other approaches could also be utilized to determine phase and perform phase mapping, however.

By way of example, the phase calculator 16 can be programmed to compute the phase by converting each cycle of electrical signal into a periodic signal as a function of time. For example, let $-\pi$ be an arbitrary beginning of the cycle; then $\pi$ is the beginning of the next cycle. The phase calculator 16 can assign each point in time in between the beginning and end of each cycle a phase value between $[-\pi,$ $\pi]$ in an increasing manner. For instance, assume that the obtained phase is the phase of a complex number of magnitude 1; that way, each respective cycle can be converted into one circle with center at 0,0 in the complex space.

In order to facilitate conversion of the signal into a corresponding phase signal, the phase calculator (or other functions) 16 can be configured to perform preprocessing on the measured electrical signals, such as to remove noise, irrelevant oscillation of the signals and to extract the salient features of the input signal, thereby increasing the accuracy and reproducibility of phase computation. In some examples, the preprocessing can be performed on acquired electrical signals such that the electrical data 14 corresponds to pre-processed (e.g., denoised) signals. In other examples, the phase calculator can be programmed to perform such preprocessing on the electrical data prior to determining phase.

The phase calculator 16 can compute the phase information for several time intervals at various points in time to make the analysis robust in terms of temporal and spatial consistency. The phase information from multiple data segments can be combined. In other examples, the time segments can span a continuous time interval. In some examples, such as for where the electrical data corresponds to or is derived from non-invasively acquired electrical signals, the phase calculator 16 can provide corresponding phase data for each location (e.g., about 2000 or more points) on the cardiac envelope for one or more time intervals for which the electrical data has been acquired. Since the electrical signals can be measured concurrently across a geometric region (e.g., over up to the entire heart surface), the computed phase data and resulting wave front likewise are spatially and temporally consistent across the geometric region of interest.

The computed phase information provided by the phase calculator 16 can be stored in memory (e.g., as phase data) and utilized by a wave front analyzer 18 to characterize one or more wave fronts on the geometric surface. For example, the wave front analyzer 18 can identify locations on the geometric surface corresponding to one or more wave fronts based on the phase data and the electroanatomic data. In the example of FIG. 1, the wave front analyzer 18 includes an activation/depolarization calculator 20 that can be programmed to compute one or both the activation or depolarization time for each respective node (e.g., on the mesh corresponding to the geometric surface).

As an example, each of the activation time or depolarization time can be determined to begin at a time where the phase signal for a given point (e.g., node on a geometric surface) crosses a chosen phase value $\phi_s$, which can define a phase threshold. The phase threshold $\phi_s$ for determining an activation or depolarization boundary condition can be fixed for a given application or it can be programmable, such as in response to a user input. Any one or more phase thresholds can be set as $\phi_s$ to identify a wave front boundary for a given time, such as can be set by a phase selector 22. In some examples, the phase threshold can be a predetermined phase value, such as can correspond to a beginning of activation or depolarization. In other examples, the phase threshold can be set to another certain stage of activation cycle, and at least one predetermined phase values can be used simultaneously. Thus, for a given graphical map that is being generated, one or more different phase thresholds $\phi_s$ can be selected to generate a corresponding number of wave fronts that can be visualized in the resulting map 12. The time can be used for indexing the phase data and the electrical data for further analysis and wave front detection.

Figure 2:
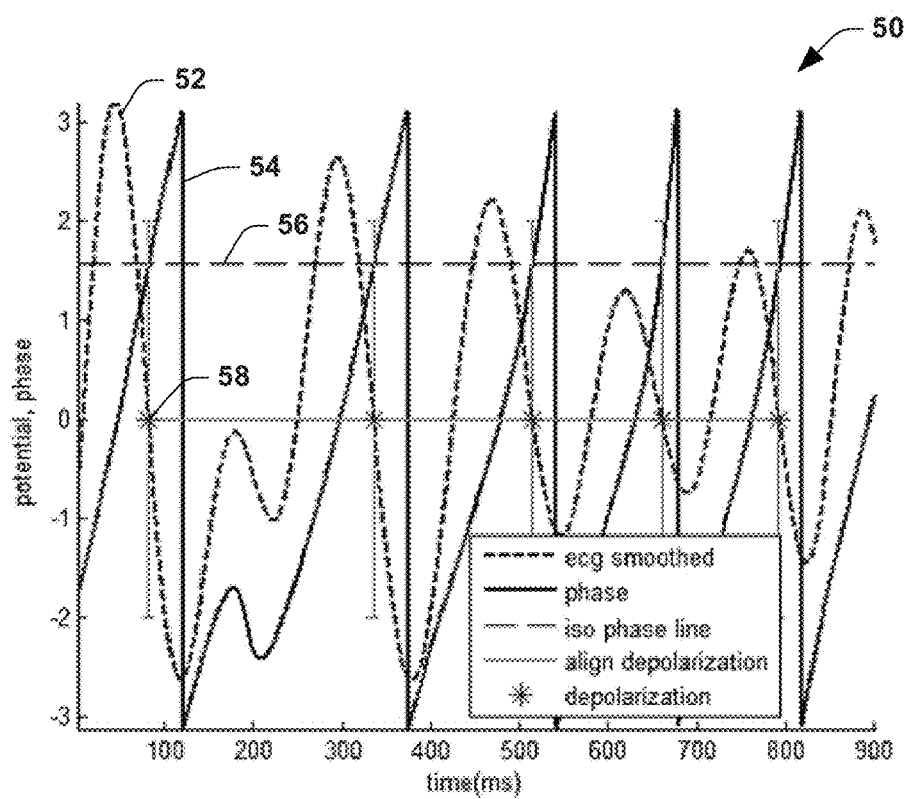
FIG. 2 depicts an example of a graph of potential and phase plotted as a function of time.

As a further example, FIG. 2 depicts a graph plotting a smoothed (e.g., preprocessed) electrocardiogram signal 52 and a phase signal 54 derived (e.g., by phase calculator 16) for the ECG signal for a time interval. In this example, the time interval includes about five cycles of the ECG and phase signals. Additionally, the selected phase $\phi_s$ for a depolarization time is demonstrated at 56 (e.g., set by phase selector 22). Thus, the time when the phase signal 54 crosses the selected phase 56 each cycle of defines a depolarization time 58 for the given node. The depolarization time and computed phase values and respective time indices can be stored in memory for each node for each cycle. Corresponding time indices can be computed for phase signals for each of the nodes across the surface region of interest and for each of a plurality of time intervals.

Referring back to FIG. 1, the wave front analyzer 18 further can determine which pairs of adjacent nodes across the surface have phase values encompassing the selected phase value $\phi_s$ the selected phase value at a given time index. In this context, the term encompass means that the selected phase value $\phi_s$ lies at or between the phase values for such pair of nodes. The term adjacent nodes can refer to nodes that are interconnected to each other by an edge of a meshed surface, for example, or be located within a predetermined distance of each other. For the example where the geometric surface is represented as a mesh of nodes interconnected by edges, the wave front analyzer 18 can determine if the selected phase value $\phi_s$ is between the phase values $\phi_i$ and $\phi_j$ for a pair of adjacent nodes i and j connected by a common edge of the mesh (e.g., $\phi_i \leq \phi_s \leq \phi_j$ or $\phi_i \geq \phi_s \geq \phi_j$). This determination can be repeated for each interconnected node pair across the geometric surface of interest to identify node pairs that encompass the wave front for one or more time intervals. As mentioned, for example, the selected phase $\phi_s$ can correspond to a phase to represent an activation time or depolarization time.

The wave front analyzer 18 further can determine a location for the wave front across the geometric surface for each time index. For example, the wave front location at a given time resides on a path extending between each of the node pairs identified as encompassing the selected phase value $\phi_s$. Where the geometric surface is a mesh, for example, the wave front analyzer 18 can determine a least one location on the geometric surface as residing on a common edge that extends between each pair of nodes that encompass selected phase $\phi_s$. The location on such common edge can be estimated as a midpoint between the respective nodes. In other examples, the location on each common edge can be computed to estimate the location of the selected phase value $\phi_s$ based on the respective values and locations of each pair of nodes.

For each time index, the wave front analyzer 18 can identify a plurality of points that estimate an activation or depolarization time across a geometric surface. These points collectively can define a wave front across the surface for each of a plurality of time indices, and the wave front analyzer 18 can connect such points to provide a corresponding wave front isochrone. For example, the wave front analyzer 18 further can be programmed to connect each of the plurality of estimated wave front points by marching through each of the edges of the mesh determined to contain the selected phase value $\phi_s$. The points through each edge can thus correspond to an intersection point of each edge. The intersection points can be connected together to represent a corresponding wave front at a given time index. For example, the resulting path of intersection points interconnecting the intersected edges can be utilized to generate a wave front isochrone for the given time index, such as corresponding to an activation wave front or depolarization wave front according to the selected phase value $\phi_s$. The wave front analyzer 18 can provide wave front data 24 that can specify the points corresponding to the selected phase $\phi_s$ for each time index in one or more intervals. Additionally or alternatively, the wave front analyzer 18 can provide wave front data 24 to data representing the isochrones connecting such points. In other examples, the isochrones may be generated from the points by a map generator 26.

The map generator 26 can generate one or more graphical maps 12 based on the wave front data 24 and geometry data 28, which defines the geometric surface for which the map is generated. For example, the map generator 26 can generate the graphical map 12 as including a graphical representation of the wave front isochrone superimposed on a graphical representation of the geometric surface. The map generator 26 can generate the graphical map 12 to graphically depict one or more locations on the geometric surface corresponding to an activation wave front or depolarization wave front. Wave front lines corresponding to different phase values (e.g., as configured by selector 12) can be generated and visualized concurrently in the graphical map 12 for the geometric surface. As mentioned the wave front data 24 can include information describing locations of a given wave on geometric surface of interest front over a plurality of time indices within one or more time intervals. Thus, the map generator can create a graphical map for each of the time indices. For example, presentation of the graphical maps in a sequence in an order of the time indices can demonstrate movement of the wave front across the geometric surface. While in the example of FIG. 1 the wave front analyzer 18 is demonstrated as being separate from the map generator 26, in other examples, the wave front analyzer could be implemented as a module (e.g., machine readable instructions) that is part of the map generator.

The electrical data 14 can include electrical activity for nodes on a geometric surface that is defined by the geometry data 28. The geometry data 28 can represent a two-dimensional or a three-dimensional surface for the patient. For example, the geometric surface can be a body surface (e.g., an outer surface of the thorax or portion thereof) where sensors are positioned to measure electrical activity. In other examples, the surface can be a surface of internal tissue or a computed envelope having a prescribed position relative to certain internal tissue. The electrical activity on the surface can be measured directly by invasive sensing means or be measured indirectly on such surface by reconstructing the electrical activity onto such surface. Depending on the geometric surface for which the electrical data 14 has been provided, the geometry data 28 can correspond to actual patient anatomical geometry (e.g., derived from one or more imaging technologies, such as xray, computed tomography, magnetic resonance imaging or the like), a preprogrammed generic model or a hybrid thereof (e.g., a model that is modified based on patient anatomy). That is, the geometric surface should represent the same surface that contains the nodes represented by the electrical data 14.

Figure 3:
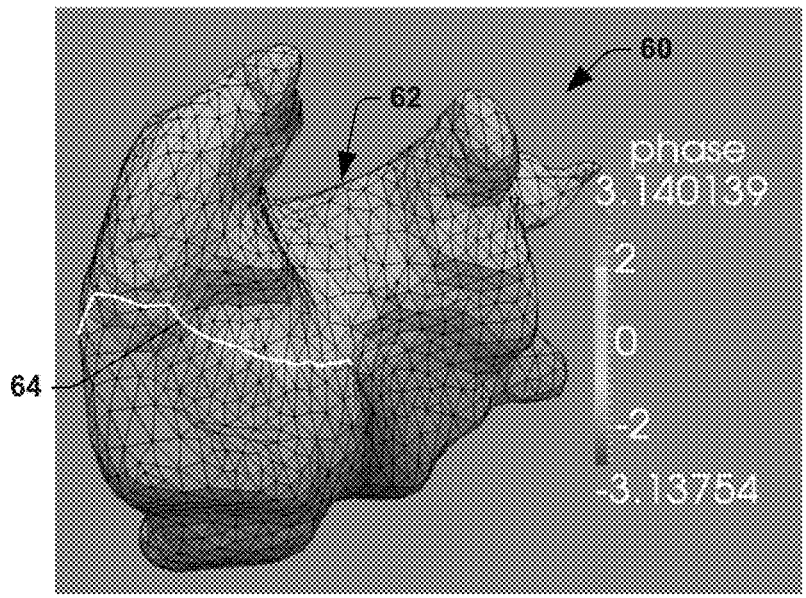
FIG. 3 depicts an example of a phase map demonstrating an isochrones line for a wave front that can be determined.

By way of illustration, FIG. 3 depicts a graphical map 60 in the form of a phase map on the geometric surface of heart 62. In the example of FIG. 3, the map 60 also includes an isochrone wave front 64, such as can be determined by the wave front analyzer 18. For example, the wave front analyzer 18 can be programmed to generate the wave front data 24 to provide one or more isochrone lines corresponding to an activation front or a depolarization front across the geometric surface of interest such as the cardiac surface 62.

Figure 4:
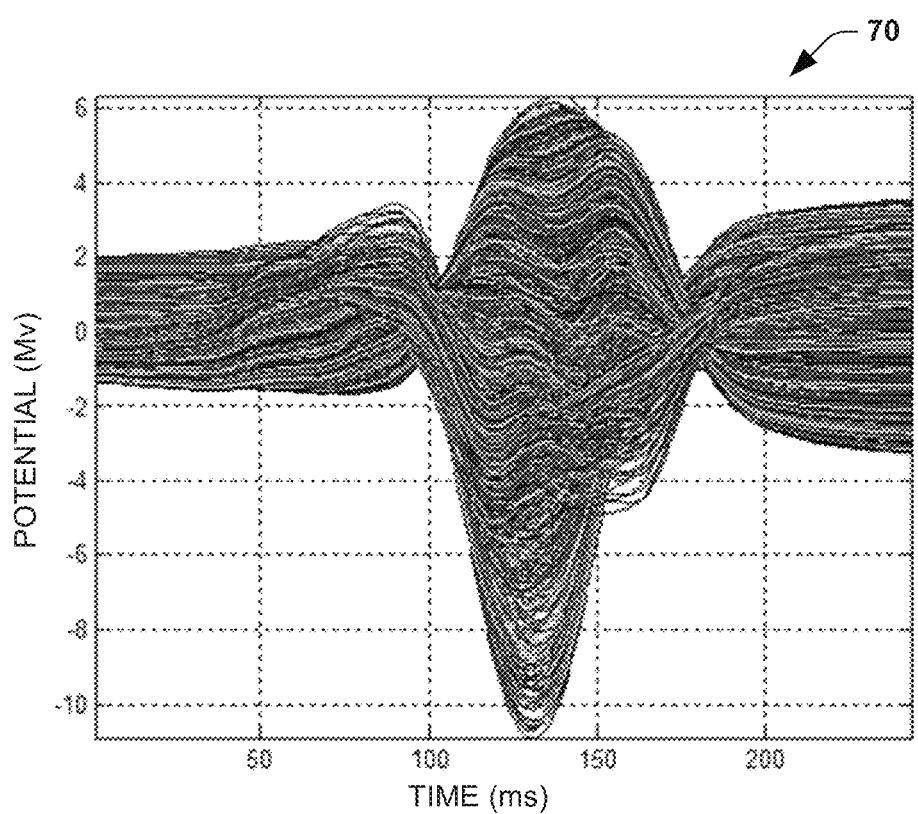
FIG. 4 depicts an example of a graph plotting electrical potential versus time demonstrating a plurality of electrograms.
Figure 5A:
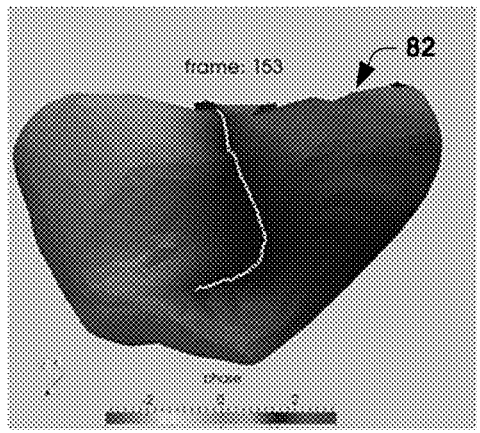
FIGS. 5A-5D depict an example of phase maps and a wave front that can be generated at different times to demonstrate movement of a wave front across a surface.
Figure 5B:
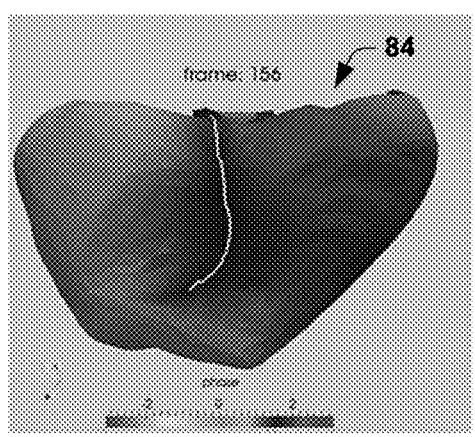
Figure 5C:
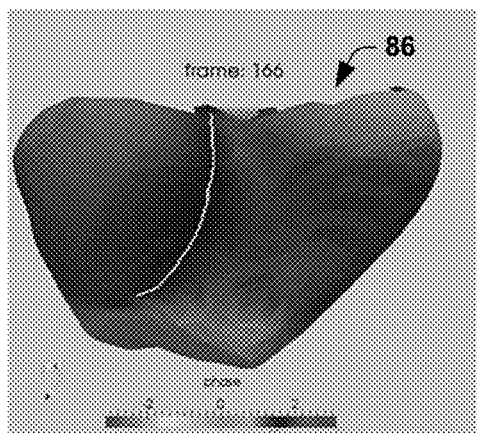
Figure 5D:
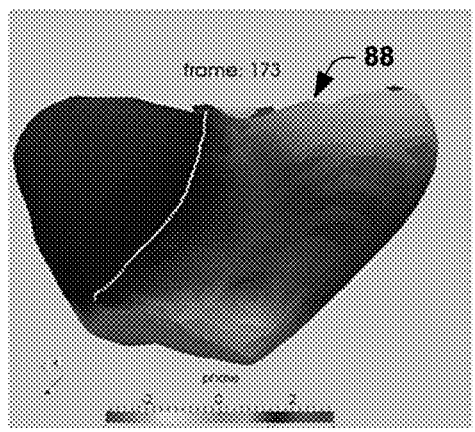

In other examples, the surface can be a body surface, such as the patient's skin where a plurality of electrodes may be positioned to measure body surface electrical activity (e.g., ECGs). FIG. 4 demonstrates an example plot of body surface electrical activity 70, such as may be measured across a region of the patient's body. FIGS. 5A, 5B, 5C and 5D demonstrate examples a set of graphical maps 82, 84, 86 and 88 that can be generated by the map generator 26 based on body surface electrical data and geometry data that represents the body surface. Each of the graphical maps 82, 84, 86 and 88 is generated to provide a wave front isochrone on the body surface for different time indices. Thus, by presenting each of the graphical maps 82, 84, 86 and 88 in a sequence according to the respective time indices movement of the wave front across the geometric surface can be visualized.

As a further example, the map generator 26 can be programmed to present a plurality of the maps 12 based on the wave front data 24, which can include static maps and/or dynamic-animated (e.g., time series of) maps. The graphical map 12 can be displayed as an integral phase at a given instant in time (a time index) for each of the locations across the geometric surface concurrently. Additionally, the map can be displayed as an animated phase map (e.g., a series of respective maps for consecutive time indices) to demonstrate temporal patterns of the phase spatially across the surface. The map generator 26 further can be configured to rotate the surface geometry (e.g., a 3-D surface) in response to a user input, such as to reveal other portions of the surface and their wave front activity according to the phase signals that have been computed at such locations, as disclosed herein. Additionally, since a property of the phase is that $-\pi$ equals $\pi$, the color coding range or other scale utilized to visualize phase can be implemented to reflect this circular property of the phase signals.

Additionally or alternatively, the map generator 26 can also generate other types of maps for evaluation, such as to facilitate diagnosis and/or treatment of an arrhythmia (e.g., fibrillation, including AF and/or VF, as well as tachycardia, including atrial tachycardia and ventricular tachycardia). Examples of some other types of maps that can be generated by the map generator 26 are disclosed in U.S. Pat. No. 8,478,393, which is incorporated herein by reference. As yet a further example, the systems and methods to perform wave front detection and related rendering in electrocardiographic maps, as disclosed herein, can be combined with other diagnostic and monitoring tools, which may include therapy delivery, to provide an integrated system. For example, the wave front analyzer 18 can be combined with a mapping system and/or a therapy system such as disclosed in the above-incorporated PCT Application No. PCT/US13/60851.

Figure 6:
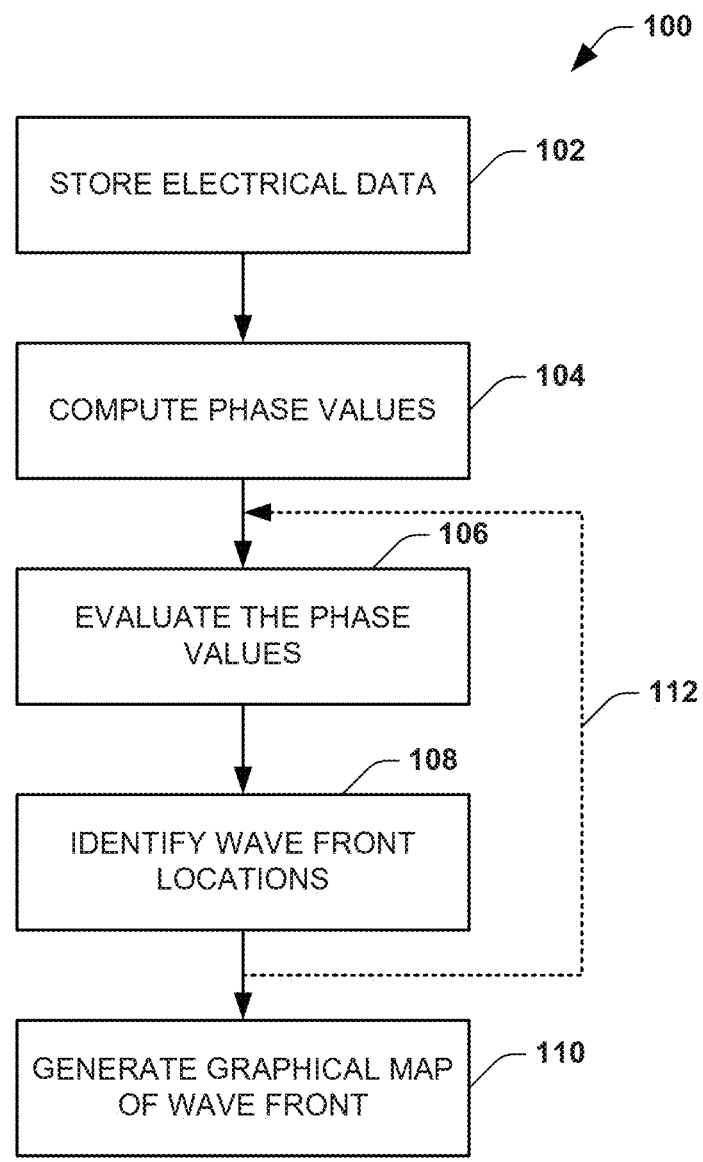
FIG. 6 is a flow diagram illustrating an example method that can be implemented to detect a wave front.

In view of the foregoing structural and functional features described above, a method that can be implemented will be better appreciated with reference to FIG. 6. While, for purposes of simplicity of explanation, the method of FIG. 4 is shown and described as executing serially, it is to be understood and appreciated that such method is not limited by the illustrated order, as some aspects could, in other embodiments, occur in different orders and/or concurrently with other aspects from that shown and described herein. Moreover, not all illustrated features may be required to implement a method. The method or portions thereof can be implemented as instructions stored in one or more non-transitory storage media as well as be executed by a processing resource (e.g., one or more processor cores) of a computer system, for example.

FIG. 6 depicts an example of a method 100 to detect a wave front of electrical activity across a geometric surface. For example, the method 100 can be implemented by the system 10 of FIG. 1. The method begins at 102 by storing electrical data (e.g., data 14 of FIG. 1) in memory. As disclosed herein, the electrical data can represent electrical activity for a plurality of nodes distributed across a geometric surface over time, which can be specified for a plurality of different time indices. At 104 phase values can be computed (e.g., by phase calculator 16) based on the electrical data to provide corresponding phase values for all or a portion of the nodes. At 106, the computed phase values can be evaluated (e.g., by the wave front analyzer 18 of FIG. 1) for at least a substantially portion of the plurality of nodes at a given time to identify each pair of adjacent nodes having phase values that encompass a wave front phase value. The wave front phase value can be fixed or selected for a given type of wave front and further may be programmable, such as in response to a user input.

At 108, wave front locations can be identified on the geometric surface as locations that reside between each pair of adjacent nodes that have been identified on the geometric surface as having phase values that encompass the wave front phase value, such as disclosed herein. At 110, one or more graphical maps can be generated (e.g., by map generator 26). Each graphical map can represent the identified wave front locations on at least a portion of the geometric surface for a respective time index. Additionally, as demonstrated schematically at 112, in some examples, the method 100 can repeat the evaluation at 106 and the identification of wave front locations at 108. For instance, these actions can be repeated for each of the time indices so that a respective graphical map can be generated based on the wave front locations identified for each of the time indices. In this way, each respective graphical map can provide a corresponding graphical representation of a wave front isochrone for a respective time index on the graphical representation of the geometric surface, such that presentation of the graphical maps in a sequence demonstrates movement of the wave front across the geometric surface.

In view of the foregoing structural and functional description, those skilled in the art will appreciate that portions of the systems and method disclosed herein may be embodied as a method, data processing system, or computer program product such as a non-transitory computer readable medium. Accordingly, these portions of the approach disclosed herein may take the form of an entirely hardware embodiment, an entirely software embodiment (e.g., in a non-transitory machine readable medium), or an embodiment combining software and hardware, such as shown and described in the Appendix. Furthermore, portions of the systems and method disclosed herein may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

What have been described above are examples. It is, of course, not possible to describe every conceivable combination of structures, components, or methods, but one of ordinary skill in the art will recognize that many further combinations and permutations are possible. Accordingly, the invention is intended to embrace all such alterations, modifications, and variations that fall within the scope of this application, including the appended claims.

Where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, and the term "including" means including but not limited to. The term "based on" means based at least in part on.

What is claimed is:

1. One or more non-transitory computer-readable media having instructions executable by at least one processor, the instructions programmed to perform a method comprising:

computing phase values for a plurality of points in time along each of a plurality of electrophysiological signals for each of a plurality of nodes distributed across a geometric surface mesh corresponding to cardiac tissue of a patient, the electrophysiological signals measured via electrodes from a patient, wherein the nodes define vertices of the geometric surface mesh and wherein adjacent pairs of vertices are each interconnected by a respective edge;

evaluating the computed phase values for each of the nodes relative to each other at a given time index and thereby identifying each pair of adjacent nodes having computed phase values for corresponding points in time of the plurality of points in time along each respective electrophysiological signal that encompass a predetermined phase value such that the predetermined phase value resides on the respective edge between each identified adjacent pair of nodes;

determining at least one location on a respective edge between each identified pair of adjacent nodes on the geometric surface mesh as corresponding to a location on a wave front at the given time index, based on the evaluating;

storing in memory wave front data identifying the determined at least one location on the geometric surface mesh; and generating a graphical map comprising a graphical representation of the wave front on a graphical representation of the geometric surface mesh corresponding to the cardiac tissue based on the wave front data.

2. The media of claim 1, wherein the at least one location comprises a plurality of locations along respective edges of the geometric surface mesh, the method further comprising connecting each of the plurality of locations and thereby providing a wave front isochrone for the geometric surface mesh at the given time index.

3. The media of claim 2, wherein the plurality of locations reside on the respective edges that interconnect each pair of adjacent nodes having phase values that encompass the predetermined phase value.

4. The media of claim 3, wherein the method further comprises connecting the plurality of locations by marching through the edges on which the each of the plurality of locations reside and thereby defining the wave front isochrone.

5. The media of claim 2, wherein generating a graphical map comprises generating a graphical representation of the wave front isochrone on the graphical representation of the geometric surface mesh.

6. The media of claim 5, wherein the graphical map further comprises a phase map of the geometric surface mesh based on the computed phase values for the given time index.

7. The media of claim 1, wherein the geometric surface mesh represents one of a body surface, an epicardial region or an endocardial region.

8. The media of claim 1, wherein the method further comprises repeating the evaluating and the determining for a plurality of time indices and thereby determining a plurality of locations on the geometric surface mesh that satisfy the predetermined phase value of the wave front for each of the plurality of time indices.

9. The media of claim 8, further comprising generating a graphical map for each of the plurality of time indices, each graphical map comprising a graphical representation of the wave front isochrone for a respective time index on a graphical representation of the geometric surface mesh.

10. The media of claim 1, wherein the predetermined phase value is set to specify at least one of an activation time or a depolarization time for the wave front based on the computed phase values.

11. The medium of claim 1, wherein the electrophysiological signals correspond to electrical signals measured non-invasively by the electrodes.

12. A system comprising:

memory to store machine readable instructions and data, the data comprising electrical data representing a plurality of electrophysiological signals measured via electrodes from a patient for a plurality of nodes distributed across a geometric surface mesh corresponding to cardiac tissue of the patient over time, wherein the nodes define vertices of the geometric surface mesh and wherein adjacent pairs of vertices are each interconnected by a respective edge, and at least one processor to access the memory and execute the instructions, the instructions comprising:

a wave front analyzer programmed to evaluate phase values for each of the plurality of nodes relative to each other at a given time index and to identify wave front locations residing on edges on the geometric surface mesh by identifying each pair of adjacent nodes having computed phase values for corresponding points in time of a plurality of points in time along each respective electrophysiological signal that encompass a predetermined phase value such that the predetermined phase value resides on the respective edge between each identified adjacent pair of nodes, the wave front analyzer further programmed to store wave front data in the memory to identify the wave front locations on the geometric surface mesh that reside between identified pairs of adjacent nodes on the geometric surface mesh, and
a map generator programmed to generate a graphical map comprising a graphical representation of the wave front on a graphical representation of the geometric surface mesh corresponding to the cardiac tissue based on the wave front data.

13. The system of claim 12, wherein the instructions further comprise a phase calculator programmed to compute the phase values for each of the plurality of nodes based on electrical data.

14. The system of claim 12, wherein the instructions further comprise a phase selector programmed to set the predetermined phase value to thereby define a type of wave front.

15. The system of claim 12, wherein the map generator is programmed to generate the graphical map that provides the graphical representation of the wave front and the graphical representation of the geometric surface mesh based on the wave front data and based on geometry data stored in the memory.

16. The system of claim 15, wherein the graphical map further comprises a phase map for the geometric surface mesh generated by the map generator based on the phase values for the given time index and the geometry data.

17. The system of claim 15, wherein the wave front analyzer is programmed to determine the wave front locations on the geometric surface mesh that have the predetermined phase value for each of a plurality of time indices, the wave front locations for each of the time indices being stored in the wave front data, and
wherein the map generator is programmed to generate a respective graphical map for each of the time indices based on the wave front data and the geometry data, each respective graphical map comprising a corresponding graphical representation of the wave front for a respective time index on the graphical representation of the geometric surface mesh.

18. The system of claim 12, wherein the geometric surface mesh is represented by geometry data stored in the memory.

19. The system of claim 18, wherein the wave front analyzer is further programmed to determine a wave front isochrone on the geometric surface mesh by marching through the edges on which the each of the plurality of wave front locations reside.

20. The system of claim 12, further comprising the electrodes configured to measure electrical signals from the patient's body non-invasively, the electrophysiological signals corresponding to the measured electrical signals.

21. A system comprising:
memory storing machine readable instructions and electrical data, the electrical data representing a plurality of electrophysiological signals measured via electrodes from a patient for a plurality of nodes distributed across a geometric surface mesh corresponding to cardiac tissue of the patient overtime, wherein the nodes define vertices of the geometric surface mesh and wherein adjacent pairs of vertices are each interconnected by a respective edge, and
at least one processor to access the memory and execute the machine readable instructions, the stored instructions comprising:
evaluating phase values computed for at least a substantial portion of the plurality of nodes at a given time index to thereby identify each pair of adjacent nodes having phase values for corresponding points in time of a plurality of points in time along each respective electrophysiological signal that encompass a wave front phase value such that the wave front phase value resides on the respective edge between each identified adjacent pair of nodes;
identifying wave front locations on the geometric surface mesh that reside between each identified pair of adjacent nodes on the geometric surface mesh; and
generating a graphical map representing the identified wave front locations on at least a portion of the geometric surface mesh corresponding to the cardiac tissue at the given time index.

22. The system of claim 21, wherein the machine readable instructions further comprise:
repeating the identifying to thereby determine the wave front locations on the geometric surface mesh that have the predetermined phase value for each of a plurality of time indices;
generating respective graphical maps each based on the wave front locations identified for each of the time indices, each respective graphical map comprising a corresponding graphical representation of the wave front isochrone for a respective time index on the graphical representation of the geometric surface mesh;
presenting each graphical map in a sequence; and thereby demonstrating movement of the wave front across the geometric surface mesh.

23. The system of claim 21, further comprising the electrodes configured to measure electrical signals from the patient's body non-invasively, the electrophysiological signals corresponding to the measured electrical signals.

* * * * *

UNITED STATES PATENT AND TRADEMARK OFFICE
CERTIFICATE OF CORRECTION

PATENT NO. : 10,039,464 B2
APPLICATION NO. : 14/157991
DATED : August 7, 2018
INVENTOR(S) : Remi Dubois et al.

Page 1 of 1

It is certified that error appears in the above-identified patent and that said Letters Patent is hereby corrected as shown below:

In the Claims

Column 12, Line 9 Claim 21, reads "overtime" should read --over time--

Signed and Sealed this
Eighteenth Day of September, 2018

Andrei Iancu
*Director of the United States Patent and Trademark Office*